(12) United States Patent
Stenzler et al.

(10) Patent No.: US 9,585,835 B1
(45) Date of Patent: **\*Mar. 7, 2017**

(54) INHALABLE NICOTINE FORMULATIONS AND METHODS OF MAKING AND USING THE SAME

(71) Applicant: Sansa Corporation (Barbados) Inc., Worthing (BB)

(72) Inventors: Alex Stenzler, Long Beach, CA (US); Noe Zamel, Ontario (CA); Arthur Slutsky, Ontario (CA); Steven Ellis, Ontario (CA)

(73) Assignee: Sansa Corporation (Barbados) Inc., Christ Church (BB)

( * ) Notice: Subject to any disclaimer, the term of this patent is extended or adjusted under 35 U.S.C. 154(b) by 0 days.

This patent is subject to a terminal disclaimer.

(21) Appl. No.: 14/856,102

(22) Filed: Sep. 16, 2015

(51) Int. Cl.
| A61K 9/00 | (2006.01) |
| A61K 31/465 | (2006.01) |
| A24B 15/16 | (2006.01) |
| A61K 47/26 | (2006.01) |
| A61K 47/18 | (2006.01) |

(52) U.S. Cl.
CPC ............ *A61K 9/0075* (2013.01); *A24B 15/16* (2013.01); *A61K 31/465* (2013.01); *A61K 47/183* (2013.01); *A61K 47/26* (2013.01)

(58) Field of Classification Search
CPC .. A61K 9/0075; A61K 31/465; A61K 47/183; A61K 47/26; A24B 15/16
See application file for complete search history.

(56) References Cited

U.S. PATENT DOCUMENTS

| 5,746,227 A | 5/1998 | Rose et al. |
| 6,234,169 B1 | 5/2001 | Bulbrook et al. |
| 6,799,576 B2 | 10/2004 | Farr |
| 8,182,838 B2* | 5/2012 | Morton ............... A61K 9/0075 424/46 |
| 8,256,433 B2 | 9/2012 | Gonda |
| 8,381,739 B2 | 2/2013 | Gonda |
| 8,440,231 B2 | 5/2013 | Smyth et al. |
| 8,668,934 B2 | 3/2014 | Vehring et al. |
| 8,689,803 B2 | 4/2014 | Gonda |
| 8,741,348 B2 | 6/2014 | Hansson et al. |
| 2003/0103908 A1 | 6/2003 | Piskorz |
| 2005/0019411 A1* | 1/2005 | Colombo ............. A61K 9/0043 424/489 |
| 2005/0211244 A1 | 9/2005 | Nilsson et al. |

(Continued)

FOREIGN PATENT DOCUMENTS

| CA | 2146954 | 10/1996 |
| CA | 2265198 | 9/1999 |

(Continued)

OTHER PUBLICATIONS

Benowitz et al., 2009, "Nicotine Chemistry, Metabolism, Kinetics and Biomarkers. Hanb. Ex. Pharmacol.," (192): 29-60.

*Primary Examiner* — Savitha Rao
(74) *Attorney, Agent, or Firm* — Riverside Law LLP

(57) ABSTRACT

The present invention provides dry powder formulations comprising nicotine, methods of using the same, and methods for making the same. The dry powder formulations may further comprise excipients, therapeutic agents, and flavor components. The dry powder formulations may be manufactured by dry processes and wet processes.

26 Claims, 6 Drawing Sheets

(56) References Cited

U.S. PATENT DOCUMENTS

| | | |
|---|---|---|
| 2007/0292519 A1 | 12/2007 | Piskorz |
| 2008/0020048 A1 | 1/2008 | Snape et al. |
| 2011/0082076 A1 | 4/2011 | Dellamary et al. |
| 2011/0268809 A1 | 11/2011 | Brinkley et al. |
| 2012/0042886 A1 | 2/2012 | Piskorz |
| 2012/0138056 A1 | 6/2012 | Morton et al. |
| 2013/0017259 A1* | 1/2013 | Azhir ................ A61K 31/465 424/461 |
| 2013/0098377 A1 | 4/2013 | Borschke et al. |
| 2013/0177646 A1 | 7/2013 | Hugerth et al. |
| 2013/0209540 A1 | 8/2013 | Duggins et al. |
| 2013/0323179 A1 | 12/2013 | Popov et al. |
| 2014/0166027 A1 | 6/2014 | Fuisz et al. |
| 2014/0212504 A1 | 7/2014 | Weers et al. |
| 2014/0234392 A1 | 8/2014 | Hansson et al. |
| 2015/0031609 A1 | 1/2015 | Steiner et al. |
| 2015/0283070 A1* | 10/2015 | Stenzler ............... A61K 9/0075 424/489 |

FOREIGN PATENT DOCUMENTS

| | | |
|---|---|---|
| WO | 2005/107872 | 11/2005 |
| WO | 2015/166344 | 11/2015 |
| WO | 2015/166350 | 11/2015 |

\* cited by examiner

| Formulation | Total Nicotine Dose | Total Amount | Percent Nicotine | Percent Leucine | Percent Lactose | Percent Menthol |
|---|---|---|---|---|---|---|
| 1 | 1 mg | 20 mg | 5% | 5% | 90% | 0% |
| 2 | 1 mg | 20 mg | 5% | 5% | 85% | 5% |
| 3 | 1 mg | 20 mg | 5% | 5% | 70% | 20% |

Figure 3

| Formulation | Total Nicotine Dose | Total Amount | Percent Nicotine | Percent Leucine | Percent Lactose | Percent Menthol |
|---|---|---|---|---|---|---|
| 4 | 1 mg | 20 mg | 5% | 5% | 80% | 10% |
| 5 | 0.5 mg | 20 mg | 2.5% | 5% | 82.5% | 10% |
| 6 | 0.3 mg | 20 mg | 1.5% | 5% | 83.5% | 10% |

- 410 Form nicotine-lactose-leucine flowable mixture
- 412 Atomize nicotine-lactose-leucine flowable mixture
- 414 Form nicotine-lactose-leucine-menthol flowable mixture
- 416 Atomize nicotine-lactose-leucine-menthol flowable mixture
- 420 Dry atomized mixture via spray drier to form mixture particles
- 430 Separate and remove particles above a particle size threshold
- 440 Separate and remove particles below a particle size threshold
- 450 Final dry powder formulation
- 460 Optionally add flavor component

400

INHALABLE NICOTINE FORMULATIONS AND METHODS OF MAKING AND USING THE SAME

BACKGROUND OF THE INVENTION

Smoking is an addictive habit which has been determined to be a contributory or causative factor in a number of diseases including respiratory diseases such as emphysema, chronic bronchitis, lung infections and lung cancer, but also in various cardiac pathologies. With an increased public awareness of the deleterious effects of smoking on human health, came an increase in the numbers of smokers trying to quit the habit. It is now largely accepted in the scientific and medical community that the nicotine in cigarette smoke creates addiction through the effects it has on brain nicotine receptors. Most regular smokers become addicted to, or dependent upon, the pharmacological effects of nicotine in tobacco smoke. A common strategy in overcoming nicotine addiction in general, and nicotine cravings in particular, is the mimicking of cigarette smoking's effects, followed by gradual reduction and, eventually, by complete elimination.

There are several effects of smoking which a potential therapeutic formulation or method would seek to mimic. Among the most important effects of smoking are the chemical and mechanical impact of cigarette smoke on the airways of the smoker, and the absorption of nicotine into the smoker's blood. The chemical and mechanical impact of cigarette smoke on the airways of the smoker results in a certain level of satisfaction experienced by the smoker. The absorption of nicotine into the smoker's blood results in nicotine reaching various receptors in the nervous system of the smoker, which in turn affects the perceived nicotine cravings experienced by the smoker. Both effects can potentially be mimicked by the administration of nicotine formulations doses to a subject seeking smoking cessation therapy. By gradually reducing the doses, until complete elimination, nicotine addiction can be treated.

Leucine is an amino acid having an aliphatic isobutyl side chain. As a result, leucine is typically classified as a hydrophobic amino acid. Leucine is an essential amino acid because the human body cannot synthesize it and it must be provided from extraneous sources. Leucine has various metabolic roles, and participates, inter alia, to the formation of sterols and to the stimulation of muscle protein synthesis. Lactose is a disaccharide found in milk, having two residues: a galactose and a glucose. Lactose is used in pharmaceutical applications, for example as a filler, due to its physical properties (e.g., compressibility). Tartaric acid is a diprotic acid, occurring naturally in many plants, for example grapes and bananas. Tartrates are salts of tartaric acid with basic compounds, such as nicotine.

Menthol is a known and widely used topical analgesic, decongestant, and cough suppressant. Almost all cigarettes contain menthol in order to adjust flavoring and reduce coughing. When the menthol concentration in cigarettes exceeds 3%, then it is labeled as a menthol cigarette. Methods of using menthol in cigarettes include addition to the tobacco leaf. A plastic ball filled with menthol can be stored in the filter of a cigarette, and then crushed prior to smoking the cigarette. Upon lighting up the cigarette, the heated smoke acts to volatilize and carry the menthol into the airways of the smoker.

There is a need in the art for improved formulations of nicotine, especially dry powder formulations suitable for inhalation. The present invention meets this need.

SUMMARY OF THE INVENTION

A dry powder nicotine formulation suitable for inhalation is described. The formulation includes nicotine, at least one sugar, and at least one amino acid. In one embodiment, the nicotine includes at least one nicotine salt. In another embodiment, the at least one nicotine salt is nicotine tartrate. In another embodiment, the concentration of nicotine is between about 0.5% and about 10%. In another embodiment, the concentration of nicotine is about 0.5%. In another embodiment, the concentration of nicotine is about 1%. In another embodiment, the concentration of nicotine is about 1.5%. In another embodiment, the concentration of nicotine is about 2%. In another embodiment, the concentration of nicotine is about 2.5%. In another embodiment, the concentration of nicotine is about 3%. In another embodiment, the concentration of nicotine is about 3.5%. In another embodiment, the concentration of nicotine is about 4%. In another embodiment, the concentration of nicotine is about 4.5%. In another embodiment, the concentration of nicotine is about 5%. In another embodiment, the concentration of nicotine is about 10%. In one embodiment, the at least one sugar is lactose. In one embodiment, the concentration of lactose is between about 50% and about 80%. In another embodiment, the concentration of lactose is between about 50% and about 99%. In another embodiment, the concentration of lactose is at least about 50%. In one embodiment, the at least one amino acid is leucine. In one embodiment, the concentration of leucine is between about 0.5% and about 10%. In one embodiment, the formulation further includes at least one flavor component. In one embodiment, the formulation further includes at least one therapeutic agent. In one embodiment, the at least one therapeutic agent is a cough suppressant. In one embodiment, the formulation further includes menthol. In one embodiment, the concentration of menthol is between about 0.5% and about 20%. In one embodiment, the formulation further includes mint. In one embodiment, the concentration of mint is between about 0.5% and about 20%.

A method of controlling the amount of nicotine and the amount of menthol in a formulation to be inhaled by a subject is also described. The method includes the steps of identifying the desired concentration of nicotine in the formulation; identifying the desired total dose of nicotine in the formulation; identifying the desired concentration of menthol in the formulation; identifying the desired total dose of menthol in the formulation; and providing the subject with an amount of formulation comprising nicotine particles and menthol particles, the formulation having the identified desired concentration of nicotine and the identified desired concentration of menthol, such that the total amount of nicotine particles in the amount of formulation equals the identified total dose of nicotine, and the total amount of menthol particles in the amount of formulation equals the identified total dose of menthol. In one embodiment, the nicotine includes at least one nicotine salt. In another embodiment, the at least one nicotine salt is nicotine tartrate. In one embodiment, the formulation further includes at least one sugar. In one embodiment, the at least one sugar is lactose. In one embodiment, the formulation further includes at least one amino acid. In one embodiment, the at least one amino acid is leucine. In one embodiment, the formulation further includes at least one therapeutic agent. In one embodiment, the formulation further includes at least one flavor component. In one embodiment, the formulation is delivered to a subject via a dry powder inhaler.

A method of delivering variable dosages of nicotine to a subject over a number of doses while maintaining a constant amount of menthol per inhalation for each dose is also described. The method includes the steps of identifying a desired concentration of nicotine in a nicotine formulation having a base menthol concentration; providing a first dose comprising an amount of formulation comprising nicotine particles having the identified concentration of nicotine and menthol particles having the base menthol concentration; and providing at least one additional dose comprising an amount of a formulation comprising nicotine particles, wherein the at least one additional dose comprises more nicotine particles than the formulation in the first dose, or less nicotine particles than the formulation in the first dose, and comprises the same base menthol concentration in the first dose. In one embodiment, the nicotine includes at least one nicotine salt. In one embodiment, the at least one nicotine salt is nicotine tartrate. In one embodiment, the formulation further includes at least one sugar. In another embodiment, the at least one sugar is lactose. In one embodiment, the formulation further includes at least one amino acid. In one embodiment, the at least one amino acid is leucine. In one embodiment, the formulation further includes at least one therapeutic agent. In one embodiment, the formulation further includes at least one flavor component. In one embodiment, the formulation is delivered to a subject via a dry powder inhaler.

A kit for delivering a dry powder nicotine formulation is also described. The kit includes at least an amount of a nicotine formulation including nicotine particles, and an instruction material.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 3 is a chart depicting exemplary formulations of the present invention delivering constant amounts of nicotine while increasing the amount of menthol.

FIG. 4 is a chart depicting exemplary formulations of the present invention delivering decreasing amounts of nicotine while maintaining a constant amount of menthol.

FIG. 6 is a flowchart depicting an exemplary method of manufacturing a formulation of the present invention comprising wet mixing.

DETAILED DESCRIPTION

Figure 1:
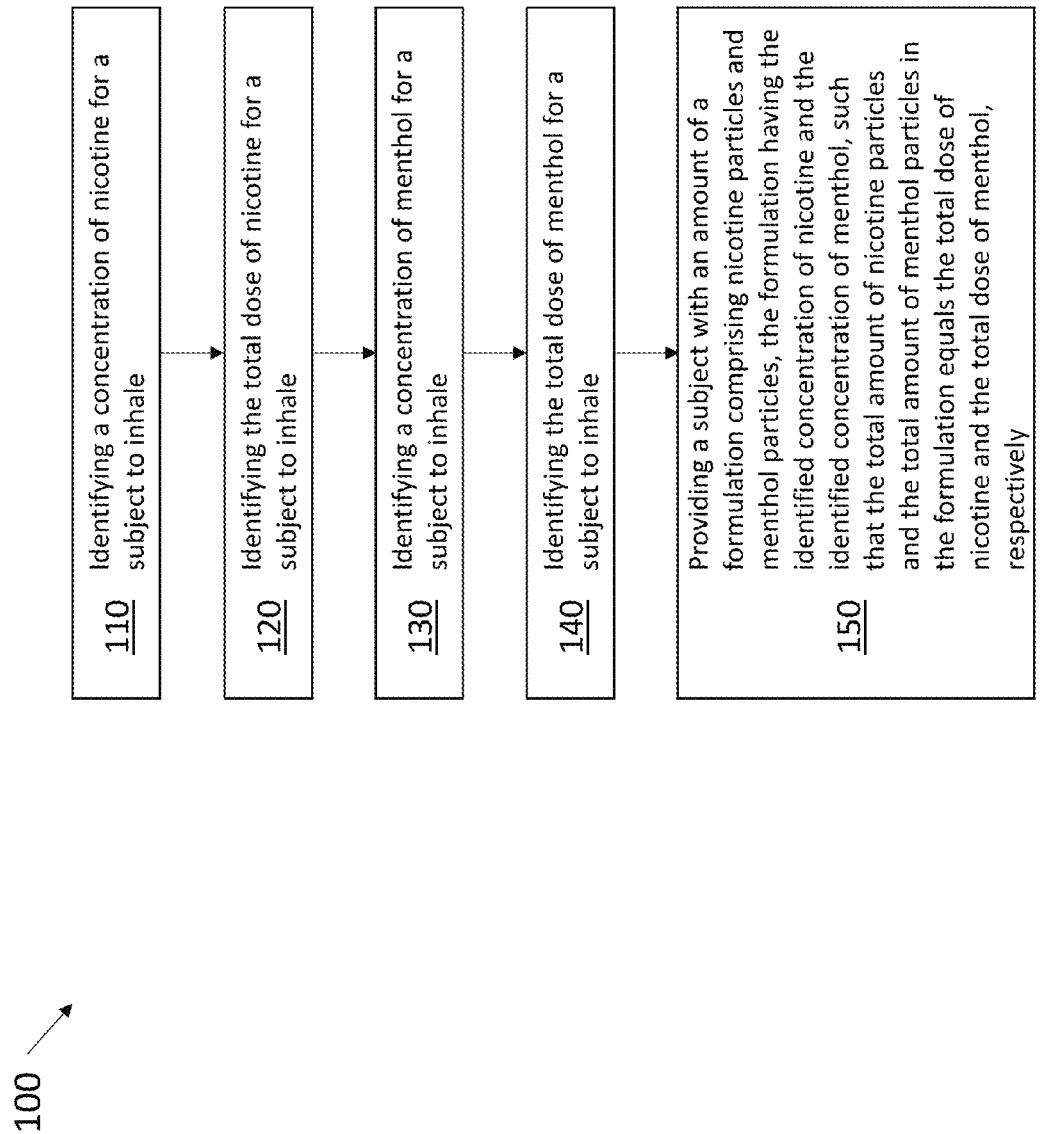
FIG. 1 is a flowchart depicting an exemplary method for delivering a desired amount of nicotine and a desired amount of menthol to a subject.

The present invention provides dry powder formulations comprising nicotine, methods for using the same, and methods for making the same. The dry powder formulations may further comprise excipients, therapeutic agents, and flavor components. The dry powder formulations may be manufactured by dry processes and wet processes.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

As used herein, the term "composition" refers to a mixture of at least one compound or molecule useful within the invention with one or more different compound, molecule, or material.

As used herein the term "formulation amount" refers to the total or partial amount of a dry powder nicotine formulation packed in a disposable container, such as a capsule or blister pack, to be used with a dry powder inhaler, or to the total or partial amount of a bulk dry powder nicotine formulation that can be loaded into a delivery chamber or compartment of a dry powder inhaler.

As used herein the term "inhalation" refers to the act of inhaling an amount of a nicotine dry powder formulation, typically from a dry powder inhaler, and can mean for example a single inhalation, or multiple inhalations.

As used herein, an "instructional material" includes a physical or electronic publication, a recording, a diagram, or any other medium of expression which can be used to communicate the usefulness of the composition and method of the invention for its designated use. The instructional material of the kit of the invention may, for example, be affixed to a container which contains the composition or be shipped together with a container which contains the composition. Alternatively, the instructional material may be delivered separately from the container with the intention that the instructional material and the composition be used cooperatively by the recipient.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable" may also refer to a carrier, meaning a medium that does not interfere with the effectiveness of the biological activity of the active ingredient(s) and is not toxic to the host to which it is administered. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

Unless stated otherwise, the described size or size range of a particle should be considered as the mass median aerodynamic diameter (MMAD) of the particle or set of particles. Such values are based on the distribution of the aerodynamic particle diameters defined as the diameter of a sphere with a density of 1 gm/cm$^3$ that has the same aerodynamic behavior as the particle which is being characterized. Because the particles described herein may be in a variety of densities and shapes, the size of the particles is expressed as the MMAD and not the actual diameter of the particles.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Compositions and Compounds

In one aspect, the invention relates to a dry powder nicotine formulation suitable for inhalation. In one embodiment, nicotine is present in the formulation as a free base. In another embodiment, the formulation comprises a nicotine salt. In one such embodiment, the nicotine salt is nicotine tartrate. In another embodiment, the nicotine salt is nicotine hydrogen tartrate. In other embodiments, the nicotine salt can be prepared from any suitably non-toxic acid, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like.

In another aspect, the invention relates to a dry powder nicotine formulation suitable for inhalation further comprising a sugar. In one embodiment, the sugar is a disaccharide. In one embodiment, the disaccharide is selected from the group consisting of sucrose, lactose, maltose, trehalose, and cellobiose. In one embodiment, the sugar is lactose.

In one aspect, the invention relates to a dry powder nicotine formulation suitable for inhalation further comprising an amino acid. In one embodiment, the amino acid is selected from the group consisting of histidine, alanine, isoleucine, arginine, leucine, asparagine, lysine, aspartic acid, methionine, cysteine, phenylalanine, glutamic acid, threonine, glutamine, tryptophan, glycine, valine, pyrrolysine, proline, selenocysteine, serine, and tyrosine. In one embodiment, the amino acid is leucine.

In one aspect, the invention relates to a dry powder nicotine formulation suitable for inhalation further comprising a flavor component. In one embodiment, the flavor component is derived from natural flavoring substances, nature-identical flavoring substances, or artificial flavoring substances. Non-limiting examples of flavor components, or flavors, include banana, cherry, cinnamon, fruit, grape, orange, pear, pineapple, vanilla, wintergreen, strawberry, and mint. In one embodiment, the flavor component is menthol. In another embodiment, the flavor component is mint.

As one skilled in the art would understand, mint refers generally, but without being limited, to any and all flavors associated with the genus of plants in the family Lamiaceae. In one embodiment, mint is a natural extract. In another embodiment, mint is a commercially available formulation, such as for example Coolmint Trusil Flavouring Powder, supplied by International Flavors & Fragrances. In one embodiment, mint is one substance. In another embodiment, mint is a mixture of substances. In one embodiment, mint comprises menthol. In another embodiment, mint comprises trans-menthone. In another embodiment, mint comprises pinene. In another embodiment, mint comprises isomenthone. In another embodiment, mint comprises limonene. In another embodiment, mint comprises eucalyptol. In another embodiment, mint comprises pin-2(3)-ene. In another embodiment, mint comprises menthyl acetate. In another embodiment, mint comprises cineole. In another embodiment, mint comprises 4,5,6,7-tetrahydro-3,6-dimethylbenzofuran. In another embodiment, mint comprises pin-2(10)-ene. In another embodiment, mint comprises dipentene. In another embodiment, mint comprises d-limonene. In another embodiment, mint comprises (R)-p-mentha-1,8-diene.

In one aspect, the invention relates to a dry powder nicotine formulation suitable for inhalation further comprising a cough suppressant. In one embodiment, the cough suppressant is menthol. In another embodiment, the cough suppressant is mint.

As one skilled in the art would understand, menthol and/or mint can perform multiple roles in a formulation. In one embodiment, menthol is a flavoring component. In another embodiment, menthol is a therapeutic agent, such as for example a cough suppressant. In one embodiment, mint is a flavoring component. In another embodiment, mint is a therapeutic agent, such as for example a cough suppressant.

Formulations

The present invention relates to dry powder formulations of nicotine suitable for inhalation. In one embodiment, the formulation comprises nicotine particles. In another embodiment, the formulation further comprises excipients. In another embodiment, the formulation further comprises therapeutic agents. In another embodiment, the formulation further comprises flavor components.

As contemplated herein, any form of nicotine may be used as the nicotine-based component. Preferably the form of nicotine used is one which achieves the fast uptake into the lungs of the patient. A form of nicotine which can be formed into particles is preferable. A form of nicotine which can be milled, or co-milled with a sugar or other components can also be used. In another embodiment, the nicotine is blended with a sugar or other components. In one embodiment, the nicotine is a salt, which, at room temperature, is a solid. The nicotine may further be a pharmacologically active analog or derivative of nicotine or substance that mimics the effect of nicotine, either alone or in combination with other active substances. If the nicotine is a base, then it may be added to a liquid carrier, such as water, and mixed to produce a generally homogeneous liquid mixture, which can then be dried by various method to form a dry particulate formulation. In other embodiments a form of nicotine which is soluble in or miscible with a liquid carrier may also be used. For example, the nicotine may be a nicotine base, which, at room temperature, is a liquid that is miscible in water. Alternatively, the nicotine base may be an oil formulation.

In one aspect, the invention relates to a dry powder nicotine formulation suitable for inhalation, wherein the concentration of nicotine is between about 0.5% and about 10%. In one embodiment, the concentration of nicotine is about 0.5%. In another embodiment, the concentration of nicotine is about 1%. In another embodiment, the concentration of nicotine is about 1.5%. In another embodiment, the concentration of nicotine is about 2%. In another embodiment, the concentration of nicotine is about 2.5%. In another embodiment, the concentration of nicotine is about 3%. In another embodiment, the concentration of nicotine is about 3.5%. In another embodiment, the concentration of nicotine is about 4%. In another embodiment, the concentration of nicotine is about 4.5%. In another embodiment, the concentration of nicotine is about 5%. In another embodiment, the concentration of nicotine is about 5.5%. In another embodiment, the concentration of nicotine is about 6%. In another embodiment, the concentration of nicotine is about 6.5%. In another embodiment, the concentration of nicotine is about 7%. In another embodiment, the concentration of nicotine is about 7.5%. In another embodiment, the concentration of nicotine is about 8%. In another embodiment, the concentration of nicotine is about 8.5%. In another embodiment, the concentration of nicotine is about 9%. In another embodiment, the concentration of nicotine is about 9.5%. In another embodiment, the concentration of nicotine is about 10%.

In one embodiment, the formulation includes nicotine particles (also referred to herein as the nicotine-based component) sized substantially between about 1-10 microns, based on the MMD of the particles. In yet another embodiment, the formulation includes nicotine particles sized substantially between about 1-7 microns. In another embodiment, the formulation includes nicotine particles sized substantially between about 2-5 microns. In yet another embodiment, the formulation includes nicotine particles sized substantially between about 2-3 microns. By selectively limiting or excluding nicotine particles below about 1 micron in size, or below about 2 microns in size, the formulations of the present invention remove or at least reduce a subject's ability to exhale nicotine back into the environment, thereby effectively reducing or removing the production of the nicotine contained in second hand smoke. Further, by selectively limiting or excluding non-respirable nicotine particles, the formulations of the present invention reduce unwanted irritation caused by nicotine particles trapped in the larger airways, oro-pharynx, the glottis vocal cords and other anatomic regions more proximal or closer to the mouth. Accordingly, in some embodiments, the smallest particles within the nicotine particle size range are at least about 1 micron, at least about 1.1 microns, at least about 1.2 microns, at least about 1.3 microns, at least about 1.4 microns, at least about 1.5 microns, at least about 1.6 microns, at least about 1.7 microns, at least about 1.8 microns, at least about 1.9 microns, or at least about 2 microns. In some embodiments, the largest particles within the nicotine particle size range are no greater than about 10 microns, no greater than about 7 microns, no greater than about 6 microns, no greater than about 5 microns, no greater than about 4.5 microns, no greater than about 4 microns, no greater than about 3.5 microns, or no greater than about 3 microns. In certain embodiments, no more than about 10% of the nicotine particles are less than about 1 micron. In certain embodiments, no more than about 10% of the nicotine particles are less than about 2 microns. In other embodiments, at least 90% of the nicotine particles are less than about 10 microns. In other embodiments, at least 90% of the nicotine particles are less than about 7 microns. In other embodiments, at least 90% of the nicotine particles are less than about 5 microns. In one embodiment, no more than about 10% of the nicotine particles are less than about 1 micron and at least 90% of the nicotine particles are less than about 10 microns. In one embodiment, no more than about 10% of the nicotine particles are less than about 1 micron and at least 90% of the nicotine particles are less than about 7 microns. In one embodiment, no more than about 10% of the nicotine particles are less than about 2 microns and at least 90% of the nicotine particles are less than about 5 microns. In one embodiment, no more than about 10% of the nicotine particles are less than about 2 microns and at least 90% of the nicotine particles are less than about 3 microns.

As would be understood by a person skilled in the art, the particle size ranges described herein are not absolute ranges. For example, a nicotine particle mixture of the present invention with a size range of about 2-5 microns can contain a portion of particles that are smaller or larger than the about 2-5 microns range. In one embodiment, the particle size value as presented for any particular component of the formulations of the present invention represents a D90 value, wherein 90% of the particles sizes of the mixture are less than the D90 value. In another embodiment, the particle size range represents a particles size distribution (PSD) wherein a percentage of the particles of the mixture lie within the listed range. For example, a nicotine particle size range of about 2-5 microns can represent a mixture of nicotine particles having at least 50% of the particles in the range of about 2-5 microns, but more preferably a higher percentage, such as, but not limited to: 60%, 70%, 80%, 90%, 95%, 97%, 98% or even 99%.

It should be appreciated that the nicotine-based component particles may be spherical or of any other shape desired. In one embodiment the particles may have an uneven or a "dimpled" surface. In such embodiments, the uneven surface may increase the ability of additional components to cling to the nicotine particles and produce a uniform coating. For example, the additional component may be a therapeutic such as menthol assuring that every nicotine particle that hits a cough receptor is coated with menthol which will suppress the cough reflex. The uneven surface may also produce a relative turbulence as the particles travel through the air, thus providing the particles with aerodynamic lift. In such embodiments, particles having such shape may be more readily entrained, and to remain entrained, in the air inhaled by a subject, thereby improving the ability of the nicotine-based component particles to travel and to be retained in the alveoli and airways of the subject.

In one embodiment, the formulation includes an amino acid. In one embodiment, the amino acid is leucine. In one embodiment, leucine acts as a stabilizer, by reducing by any degree the degradation of a composition of the invention. In another embodiment, leucine prevents the degradation of a composition of the invention by acting as a buffer by virtue of its buffering capabilities. In another embodiment, leucine acts as a powder flow enhancer. In another embodiment, the leucine in a composition of the invention improves the flow of the powder. In another embodiment, the leucine in a composition of the invention causes the particles of the powder formulation to be more readily entrained, and to remain entrained, in the air inhaled by a subject, thereby improving the ability of the composition particles to travel to and to be retained in the alveoli and airways. In one embodiment, the percentage of leucine in the formulation is between 0.5% and 10%. In some embodiments, the percentage of leucine in the formulation is between 1.5% and 2.5%. In other embodiments, the percentage of leucine in the formulation is between 0.5% and 2.5%. In yet other embodiments the percentage of leucine in the formulation is between 1.5% and 5%. In one embodiment, the percentage of leucine in the formulation is about 2.5%. In another embodiment, the percentage of leucine in the formulation is about 5%. In another embodiment, the percentage of leucine in the formulation is about 7.5%. In another embodiment, the percentage of leucine in the formulation is about 10%.

In one embodiment, the formulation further comprises excipients. As contemplated herein, one embodiment of an excipient is a bulking agent. Bulking agents may include inhalable sugars that are generally solid at room temperature. The sugar can be milled into a particulate formulation, either by itself, or co-milled with a nicotine component. The sugar may also be soluble in a liquid carrier, such as water. Without limitation, examples of suitable sugars are lactose, sucrose, raffinose, trehalose, fructose, dextrose, glucose, maltose, lecithin, mannitol, or combinations thereof. In one embodiment, the sugar is lactose. In another embodiment, the lactose is coarse lactose. In another embodiment, the sugar is alpha monohydrate lactose. The sugar may be a natural or a synthetic sugar, and may include any analogs or derivatives of sugars. It should be appreciated that any form of sugar approved as an excipient may be used as a carrier in the production of the nicotine-based component. While not required, the sugar is preferably of a pharmaceutical grade as would be understood by those skilled in the art. Preferably, the pharmaceutical grade sugar used to be milled by itself, co-milled with a nicotine component or to create the flowable mixture is a non-spheronized sugar. The pharmaceutical grade sugar may be prepared in a non-spheronized form prior to dry or wet admixture with nicotine. For example, the pharmaceutical grade sugar may be first prepared in a non-spheronized form by freeze drying, milling, micronizing or the like. In certain embodiments, the pharmaceutical grade sugar may be subjected to milling, bashing, grinding, crushing, cutting, sieving or other physical degradation process as understood by those skilled in the art, which ultimately reduces the particle size of the sugar and results in a non-spheronized sugar.

It should be appreciated that there are no limitations to the ratio of nicotine to sugar used, and the actual ratio used will be based on the concentration of nicotine desired in the nicotine based component particles. Accordingly, in one embodiment the concentration of sugar is at least about 50%. In another embodiment, the concentration of sugar is between about 50% and about 99%.

In another embodiment, the formulation can further comprise an excipient that is any pharmaceutically acceptable material, composition or carrier, such as a liquid or solid filler, stabilizer, dispersing agent, suspending agent, diluent, thickening agent, solvent or encapsulating material, involved in carrying or transporting a compound useful within the invention within or to the subject such that it may perform its intended function. In one embodiment, the formulation further comprises a stabilizing agent. Each material must be "acceptable" in the sense of being compatible with the other ingredients of the formulation, including nicotine, and not injurious to the subject. Some materials that may useful in the formulation of the present invention include pharmaceutically acceptable carriers, for example sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; amino acids, such as leucine, L-leucine, D-leucine, DL-leucine, isoleucine, lysine, valine, arginine, aspartic acid, threonine, methionine, phenylalanine; alginic acid; derivatives of amino acids, such as derivative of an amino acid, for example aspartame or acesulfame K; pyrogen-free water; isotonic saline; Ringer's solution; ethyl alcohol; phosphate buffer solutions; and other non-toxic compatible substances employed in pharmaceutical formulations. Other pharmaceutically acceptable materials that can be useful in the formulation include any and all coatings, antibacterial and antifungal agents, and absorption delaying agents, and the like that are compatible with the activity of nicotine or any other compound useful within the invention, and are physiologically acceptable to the subject. Supplementary active compounds, including pharmaceutically acceptable salts of those compounds, may also be incorporated into the compositions. Other additional ingredients that may be included in the compositions used in the practice of the invention are known in the art and described, for example in Remington's Pharmaceutical Sciences (Genaro, Ed., Mack Publishing Co., 1985, Easton, Pa.), which is incorporated herein by reference.

In one embodiment, the formulation of the present invention may further comprise therapeutic agents. In one embodiment, the additional cough suppressant component is menthol. In one embodiment, the concentration of menthol in the formulation is between about 0.5% and about 20%. As contemplated herein, any form of menthol, such as a solid form of menthol can be used for processing into menthol particles, powder, solution or suspension useful within the present invention. Non-limiting examples of solid forms of menthol include powders, crystals, solidified distillate, flakes, and pressed articles. In one embodiment, menthol is in the form of crystals. Menthol can be processed into particles of a size ranging from about 5 microns (μm) to about 10 μm using any method known in the art. In some embodiments, menthol is admixed with further liquid or solid additives for processing. Particulate additives can furthermore also be used. In one embodiment, menthol is admixed with silicon dioxide. In another embodiment, menthol is admixed with a sugar, such as lactose. In some embodiments of the wet process, the menthol is processed in a liquid carrier. In another embodiment, the additional cough suppressant component is mint. In one embodiment, the concentration of mint in the formulation is between about 0.5% and about 20%. As contemplated herein, any form of mint, such as a solid form of mint can be used for processing into mint particles, powder, solution or suspension useful within the present invention.

In one embodiment, the therapeutic agent may include a cough suppressant component having particles sized substantially between 5 and 10 microns. In another embodiment, the additional cough suppressant component may include benzocaine. It should be appreciated that the additional cough suppressant component can include any compound approved for suppressing cough. By selectively including menthol particles between 5-10 microns, these non-respirable menthol particles can reduce cough in the subject's upper airways. Accordingly, in some embodiments, the smallest particles within the additional cough suppressant component particle size range are at least about 5 microns, at least about 6 microns, at least about 7 microns, or at least about 8 microns. In some embodiments, the largest particles within the additional cough suppressant component particle size range are no greater than about 10 microns, no greater than about 9 microns, no greater than about 8 microns, or no greater than about 7 microns. In certain embodiments, no more than about 10% of the additional cough suppressant particles are less than about 5 microns. In other embodiments, at least 90% of the additional cough suppressant particles are less than about 10 microns. In other embodiments, at least 90% of the additional cough suppressant particles are less than about 8 microns. In one embodiment, no more than about 10% of the additional cough suppressant particles are less than 4 microns and at least 90% of the additional cough suppressant particles are less than about 10 microns. In one embodiment, no more than about 10% of the additional cough suppressant particles are less than about 5 microns and at least 90% of the additional cough suppressant particles are less than about 8 microns. Although in the preferred embodiment the additional cough suppressant component is composed of particles substantially in the range of 5-10 microns, the additional cough suppressant component can comprise particles in a broader range. In one embodiment, the additional cough suppressant component can comprise particles in the range of 5-25 microns. In another embodiment, the additional cough suppressant component comprises particles substantially in the range of 5-50 microns. In yet another embodiment, the additional cough suppressant component comprises particles substantially in the range of 5-100 microns.

In another embodiment, the formulation of the present invention may further include an additional cough suppressant component having particles sized substantially between 10-200 microns. This additional cough suppressant component can be added to the formulation instead of, or in addition to, the additional cough suppressant component in the range of 5-10 previously discussed. Accordingly, the formulation of the present invention can comprise two additional cough suppressant components, wherein each additional cough suppressant component has a substantially different particle size distribution. The 10-200 micron additional cough suppressant component may reduce a cough caused by irritation of the oro-pharynx, the glottis vocal cords and other anatomic regions more proximal or closer to the mouth that contain receptors that can trigger cough or trigger other unwanted sensations. As contemplated herein, these larger particles are substantially prohibited from entering the sub-glottic airways. Accordingly, in some embodiments, the smallest particles within the additional cough suppressant component particle size range are at least about 10 micron, at least about 12 micron, at least about 20 micron, at least about 30 micron, or at least about 50 micron. In some embodiments, the largest particles within the additional cough suppressant component particle size range are no greater than about 200 micron, no greater than about 150 micron, no greater than about 120 micron, no greater than about 100 micron, no greater than about 90 micron, or no greater than about 80 micron. In certain embodiments, no more than about 10% of the additional cough suppressant component particles are less than about 10 micron. In certain embodiments, no more than about 10% of the additional cough suppressant component particles are less than about 20 micron. In other embodiments, at least 90% of the additional cough suppressant component particles are less than about 200 micron. In other embodiments, at least 90% of the additional cough suppressant component particles are less than about 150 micron. In other embodiments, at least 90% of the additional cough suppressant component particles are less than about 100 micron. In one embodiment, no more than about 10% of the additional cough suppressant component particles are less than 10 micron and at least 90% of the additional cough suppressant component particles are less than about 200 micron. In one embodiment, no more than about 10% of the additional cough suppressant component particles are less than about 12 micron and at least 90% of the additional cough suppressant component particles are less than about 100 micron. In one embodiment, the additional cough suppressant component includes menthol particles between about 10-200 microns in size. In another embodiment, the additional cough suppressant component having particles between about 10-200 microns in size may include benzocaine. It should be appreciated that the additional cough suppressant component having particles between about 10-200 microns in size can include any compound approved for suppressing cough. In another example, the addition of at least one component in the formulation of the present invention other than the nicotine component may act to dilute the nicotine containing particles and decrease cough caused by nicotine irritating the oro-pharynx, vocal cords and other anatomic regions proximal to the trachea.

In one embodiment, the formulations of the present invention may optionally include a flavor component having particles sized substantially between about 10-1000 microns. In one embodiment, the flavor component is composed of particles substantially in the range of about 10-200 micron. In a preferred embodiment, the flavor component is composed of particles substantially in the range of about 10-100 micron. This flavor component utilizes such embedded larger particles that may impact the subject in the oral cavity to produce a desired flavor. Further, by limiting such flavor component particles to larger than about 10 microns in size, these particles are limited in their ability to enter into the subject's lungs. Accordingly, in some embodiments, the smallest particles within the flavoring component particle size range are at least about 10 micron, at least about 12 micron, at least about 20 micron, at least about 30 micron, or at least about 50 micron. In some embodiments, the largest particles within the flavoring component particle size range are no greater than about 1000 micron, no greater than about 500 micron, no greater than about 200 micron, no greater than about 150 micron, no greater than about 120 micron, no greater than about 100 micron, no greater than about 90 micron, or no greater than about 80 micron. In certain embodiments, no more than about 10% of the flavor component particles are less than about 10 micron. In certain embodiments, no more than about 10% of the flavor component particles are less than about 20 micron. In other embodiments, at least 90% of the flavor component particles are less than about 1000 micron. In other embodiments, at least 90% of the flavor component particles are less than about 500 micron. In other embodiments, at least 90% of the flavor component particles are less than about 200 micron. In other embodiments, at least 90% of the flavor component particles are less than about 150 micron. In other embodiments, at least 90% of the flavor component particles are less than about 100 micron. In one embodiment, no more than about 10% of the flavor component particles are less than 10 micron and at least 90% of the flavor component particles are less than about 1000 micron. In one embodiment, no more than about 10% of the flavor component particles are less than 10 micron and at least 90% of the flavor component particles are less than about 200 micron. In one embodiment, no more than about 10% of the flavor component particles are less than about 10 micron and at least 90% of the flavor component particles are less than about 100 micron. In one embodiment, the flavor component is mint. In another embodiment, the flavor component is menthol. In other embodiments, the flavor component may include tobacco, fruit flavors, or food grade flavorings used in candy or baking. It should be appreciated that the flavor compound may be any flavoring compound known in the art, preferably a regulatory-approved flavoring compound.

In various embodiments, the relative weight percentage of each component in the formulation of the present invention can be varied to achieve different characteristics. Thus, as one skilled in the art would understand, the relative weight percentages of the components can be modified for various reasons, for example, but not limited to: achieving a certain level of blood nicotine concentration while modulating the level of harshness on the airways of the subject, achieving a certain level of harshness while modulating the level of satisfaction perceived by the subject of the therapy, achieving better uptake of nicotine in the lungs of the patient, achieving faster blood nicotine kinetics, optimizing the cough suppressant performance of the formulation, varying or improving the taste of the formulation, and adjusting the relative dose of nicotine. In certain embodiments, the formulation can be about 1-20% by weight flavor component, with a preferred weight of 1-5% flavor component. In certain embodiments, the formulation can be about 1% to about 10% by weight cough suppressant, with a preferred weight of about 0.5% to about 5% cough suppressant. In various embodiments, the remaining portion of the formulation, aside from any flavor components, cough suppressant components, carriers, or other components, is the nicotine component. In one embodiment, the formulation can be approximately 10% nicotine component.

In one embodiment, the percentage of lactose in the formulation is between 50% and 99%. In one embodiment, the percentage of lactose in the formulation is between 50% and 80%. In some embodiments, the percentage of lactose in the formulation is between 75% and 90%. In other embodiments, the percentage of lactose in the formulation is between 75% and 85%. In yet other embodiments the percentage of lactose in the formulation is between 80% and 90%. In yet other embodiments the percentage of lactose in the formulation is between 80% and 99%. In one embodiment, the percentage of lactose in the formulation is about 50%. In one embodiment, the percentage of lactose in the formulation is about 60%. In one embodiment, the percentage of lactose in the formulation is about 70%. In one embodiment, the percentage of lactose in the formulation is about 80%. In another embodiment, the percentage of lactose in the formulation is about 90%. In another embodiment, the percentage of lactose in the formulation is about 95%. In another embodiment, the percentage of lactose in the formulation is about 99%.

In one embodiment, the percentage of menthol in the formulation is between 0% and 20%. In some embodiments, the percentage of menthol in the formulation is between 5% and 20%. In other embodiments, the percentage of menthol in the formulation is between 5% and 15%. In yet other embodiments the percentage of menthol in the formulation is between 10% and 20%. In one embodiment, the percentage of menthol in the formulation is about 5%. In another embodiment, the percentage of menthol in the formulation is about 20%.

In one embodiment, the percentage of mint in the formulation is between 0% and 20%. In some embodiments, the percentage of mint in the formulation is between 5% and 20%. In other embodiments, the percentage of mint in the formulation is between 5% and 15%. In yet other embodiments the percentage of mint in the formulation is between 10% and 20%. In one embodiment, the percentage of mint in the formulation is about 5%. In another embodiment, the percentage of mint in the formulation is about 20%.

Methods of Use

In one aspect, the invention relates to methods for controlling the amount of nicotine and the amount of menthol inhaled by a subject, including increasing, decreasing, or maintaining the amount of nicotine and the amount of menthol in the powder formulation inhaled by a subject. For example, as shown in FIG. 1, method 100 includes the steps of identifying a concentration of nicotine for a subject to inhale 110, identifying the total dose of nicotine for a subject to inhale 120, identifying a concentration of menthol for a subject to inhale 130, identifying the total dose of menthol for a subject to inhale 140. Finally, step 150 provides a subject with an amount of a formulation comprising nicotine particles having the identified concentration of nicotine and comprising menthol particles having the identified concentration of menthol, such that the total amount of nicotine particles and menthol particles in the formulation equals the total dose of nicotine and the total dose of menthol.

Figure 2:
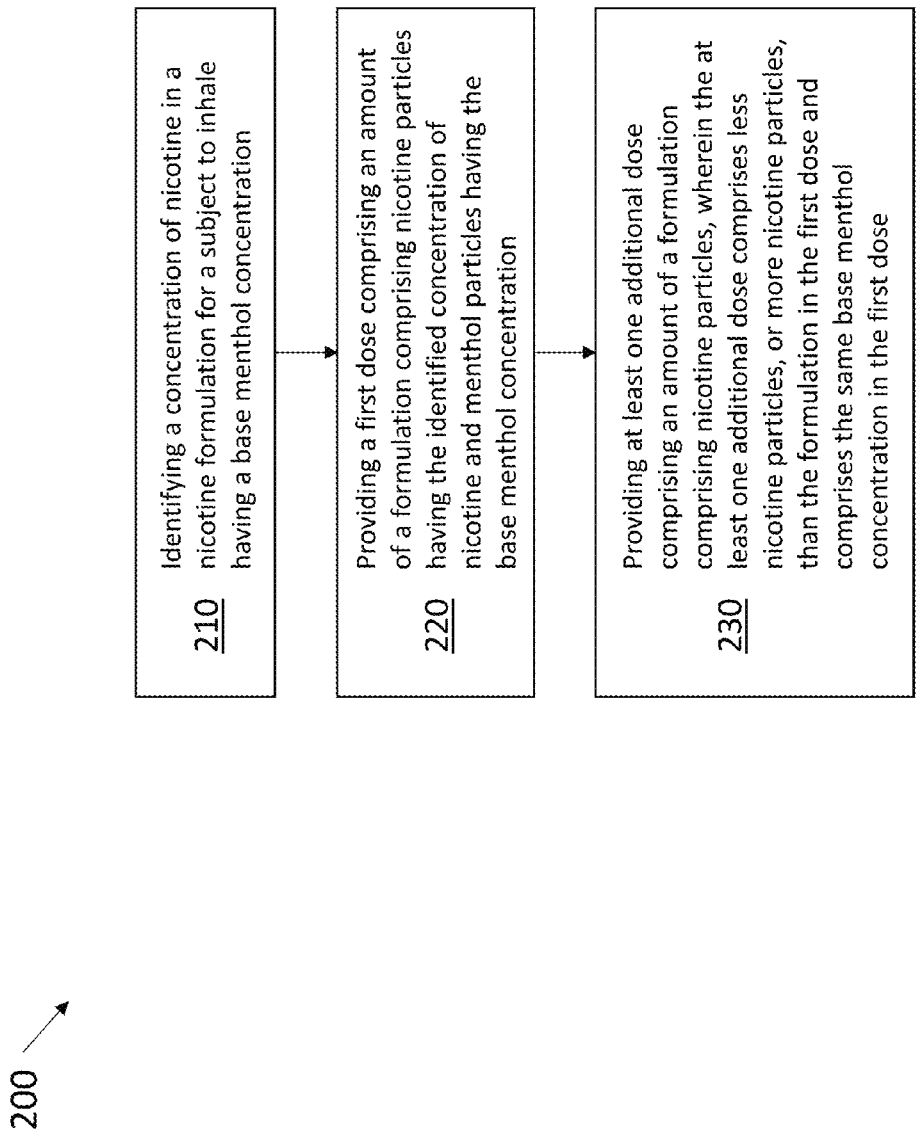
FIG. 2 is a flowchart depicting an exemplary method for delivering reduced or increased dosages of nicotine to a subject over a number of doses, while maintaining a constant level of menthol per dose.

In another embodiment, as shown in FIG. 2, method 200 comprises steps for decreasing the amount of nicotine while maintaining the amount of menthol inhaled by a subject. Method 200 includes the steps of identifying a concentration of nicotine in a nicotine formulation for a subject to inhale having a base menthol concentration 210, providing a first dose comprising an amount of a formulation comprising nicotine particles having the identified concentration of nicotine and menthol particles having the base menthol concentration 220, and providing at least one additional dose comprising an amount of a formulation comprising nicotine particles, wherein the at least one additional dose comprises less nicotine particles than the formulation in the first dose and comprises the same base menthol concentration in the first dose 230.

Referring now to FIG. 3, three different formulations are outlined, where each formulation is designed to deliver the same dose of nicotine (1 mg). To achieve a base level of nicotine delivery (Formulation 1), the total dose of nicotine forms part of a 20 mg total formulation amount of powder comprising 5% leucine and 90% lactose, which results in a nicotine concentration of 5% in the formulation. Assuming that approximately 1 mg of powder can be inhaled per a single inhalation, then about 0.05 mg of nicotine is inhaled per single inhalation, and the total dose of nicotine is administered after completion of about 20 single inhalations to take up the 20 mg of formulation powder. To achieve an increased level of menthol delivery when delivering 1 mg of nicotine, the total dose of nicotine is part of a 20 mg total formulation amount of powder comprising 5% leucine, 85% lactose, and 5% menthol, which results in a nicotine concentration of 5% (Formulation 2). Assuming that approximately 1 mg of powder can be inhaled per single inhalation, then about 0.05 mg of nicotine is inhaled per single inhalation, and the total dose of nicotine is administered after completion of about 20 single inhalations to take up the 20 mg of formulation powder. By taking up an amount of menthol per inhalation, the user experiences an increased level of cough suppression compared to Formulation 1. To achieve a further increased level of cough suppression when delivering 1 mg of nicotine, the total dose of nicotine forms part of a 20 mg total formulation amount of powder comprising 5% leucine, 70% lactose, and 20% menthol, which results in a nicotine concentration of 5% (Formulation 3). Assuming that approximately 1 mg of powder can be inhaled per single inhalation, then about 0.05 mg of nicotine is inhaled per single inhalation, and the total dose of nicotine is administered after completion of about 20 single inhalations to take up the 20 mg of formulation powder. By taking up an increased amount of menthol per inhalation, the user experiences an increased level of cough suppression compared to Formulations 1 and 2.

In another embodiment, the total dose of nicotine can be gradually reduced. For example, as shown in FIG. 4, three different formulations are outlined, where each formulation is designed to deliver a different (smaller) total dose of nicotine while maintaining the same amount of cough suppression. Starting with Formulation 4, 1 mg total dose of nicotine forms part of a 20 mg total formulation amount of powder comprising 5% leucine, 80% lactose, and 10% menthol, which results in a nicotine concentration of 5%. Assuming that approximately 1 mg of powder can be inhaled per single inhalation, this means that about 0.05 mg of nicotine is inhaled per single inhalation, and the total dose of nicotine is administered after completion of about 20 single inhalations at the initial nicotine dose. Formulation 5 is designed for delivery of a total dose of 0.5 mg of nicotine with the same level of cough suppression. Accordingly, 0.5 mg total dose of nicotine may form part of a 20 mg total formulation amount of powder comprising 5% leucine, 82.5% lactose, and 10% menthol, which results in a nicotine concentration of about 2.5%. Assuming that approximately 1 mg of powder can be inhaled per single inhalation, this means that about 0.025 mg of nicotine is inhaled per single inhalation, and the total dose of nicotine is administered after completion of about 20 single inhalations with the same level of cough suppression. Formulation 6 is designed for delivery of a total dose of 0.3 mg of nicotine with again the same level of cough suppression. Accordingly, 0.3 mg total dose of nicotine may form part of a 20 mg total formulation amount of powder comprising 5% leucine, 83.5% lactose, and 10% menthol, which results in a nicotine concentration of about 1.5%. Assuming that approximately 1 mg of powder can be inhaled per single inhalation, this means that about 0.015 mg of nicotine is inhaled per single inhalation, and the total dose of nicotine is administered after completion of about 20 single inhalations with the same level of cough suppression. Thus, a subject can gradually step down the total dose of nicotine administered by subsequently administering Formulations 4-6, while experiencing a constant level of cough suppression throughout the reduction in delivered nicotine. In one embodiment, formulations of decreasing nicotine concentrations can be used in a smoke cessation regimen. Similarly, a subject can gradually step up the total dose of nicotine administered by subsequently administering formulations of increasing nicotine concentrations, while experiencing a constant level of cough suppression throughout the increasing in delivered nicotine.

It should be appreciated that any manner of increasing, decreasing or maintaining the total dose of nicotine in a nicotine formulation can be combined with any manner of increasing, decreasing or maintaining the amount of menthol in the formulation.

As contemplated herein, there is no limitation to the particular formulation amount of powder or the concentration of nicotine within the total formulation amount, but rather, the present invention relates to the ability to alter one or both of these parameters when delivering a total dose of nicotine to a subject via a dry powder inhaler. Further, there is no limitation to the actual amount of powder inhaled per inhalation. Such amounts can be dependent on the functionality of the dry powder inhaler used, or it can be user performance dependent, where a user elects to take a shallower, or deeper, inhalation through the dry powder inhaler used. Furthermore, by administering the total dose of nicotine across multiple inhalations, the subject can more consistently insure uptake of the total dose of nicotine, as any user error occurring during a single inhalation is ultimately corrected through one or more subsequent inhalations.

Methods of Manufacture

The present invention also relates to methods of making the formulations of the present invention. In one embodiment, the methods comprise dry mixing. In one embodiment, the methods comprise wet mixing.

Figure 5:
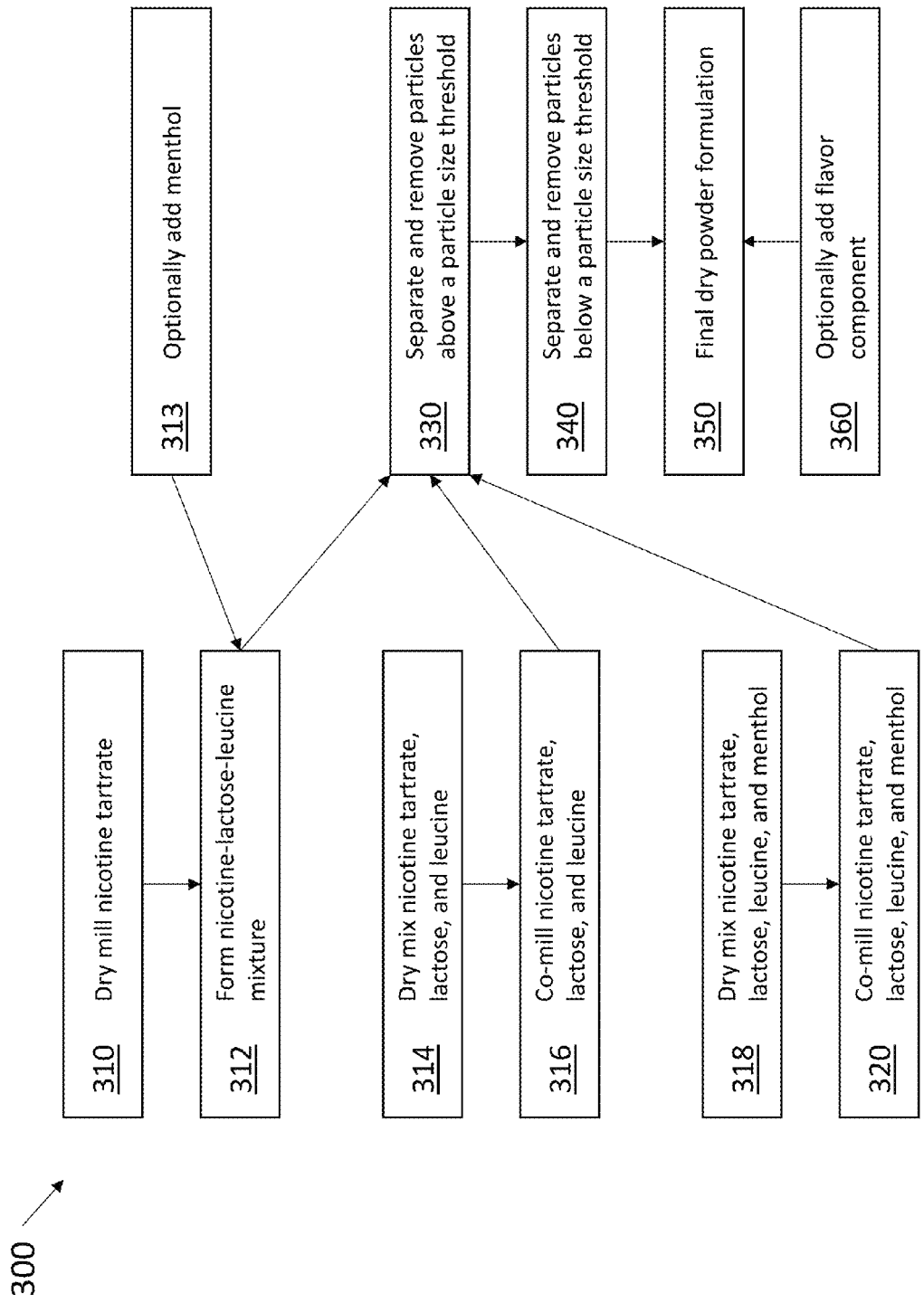
FIG. 5 is a flowchart depicting an exemplary method of manufacturing a formulation of the present invention comprising dry mixing.

Referring now to FIG. 5, an exemplary dry process or method 300 of producing any one of the formulations described herein is depicted. For example, in step 310, nicotine tartrate is dry milled. At step 312, nicotine is mixed with lactose and leucine. Optionally at step 313, a therapeutic such as menthol is added. In some embodiments, the nicotine or nicotine salt is not bound to any other components of the formulation. That is, the formulation contains distinct particles of nicotine or a nicotine salt, and distinct particles of other components of the formulation, such as a sugar. In one embodiment, the nicotine is not bound to the lactose and leucine particles. In another embodiment, the nicotine is not bound to the menthol particles. In another embodiment, the nicotine is at least partially bound to the menthol particles. Alternatively, nicotine tartrate, lactose and leucine may be first dry mixed, such as in step 314, and co-milled in step 316. In another embodiment, nicotine tartrate, lactose, leucine, and a therapeutic such as menthol are first dry mixed, such as in step 318, and co-milled in step 320. At step 330, the particles of the resulting formulation are filtered, such as with a sieve, to remove any particles larger than a threshold size value. At step 340, the particles of the resulting formulation are filtered again to remove any particles smaller than a threshold size value, resulting in the final dry powder formulation 350. In some embodiments, only one filtering step is needed. In other embodiments, two or more filtering steps are needed. Optionally at step 360, a flavor component may be added to final formulation 350. Step 360 may contain any number of processing steps needed to obtain the desired particle size (e.g., 10-1000 micron) for the flavor component being added.

Any method of blending particles in and for the methods and formulations of the present invention is contemplated here. The blending can be conducted in one or more steps, in a continuous, batch, or semi-batch process. For example, if two or more excipients are used, they can be blended together before, or at the same time as, being blended with the pharmaceutical agent microparticles.

The blending can be carried out using essentially any technique or device suitable for combining the microparticles with one or more other materials (e.g., excipients) effective to achieve uniformity of blend. The blending process may be performed using a variety of blenders. Representative examples of suitable blenders include V-blenders, slant-cone blenders, cube blenders, bin blenders, static continuous blenders, dynamic continuous blenders, orbital screw blenders, planetary blenders, Forberg blenders, horizontal double-arm blenders, horizontal high intensity mixers, vertical high intensity mixers, stirring vane mixers, twin cone mixers, drum mixers, and tumble blenders. The blender preferably is of a strict sanitary design required for pharmaceutical products.

Tumble blenders are often preferred for batch operation. In one embodiment, blending is accomplished by aseptically combining two or more components (which can include both dry components and small portions of liquid components) in a suitable container. One example of a tumble blender is the TURBULA™, distributed by Glen Mills Inc., Clifton, N.J., USA, and made by Willy A. Bachofen AG, Maschinenfabrik, Basel, Switzerland.

For continuous or semi-continuous operation, the blender optionally may be provided with a rotary feeder, screw conveyor, or other feeder mechanism for controlled introduction of one or more of the dry powder components into the blender.

A milling step is used to fracture and/or deagglomerate the blended particles, to achieve a desired particle size and size distribution, as well as to enhance distribution of the particles within the blend. Any method of milling can be used to form the particles of the invention, as understood by one of ordinary skill in the art. A variety of milling processes and equipment known in the art may be used. Examples include hammer mills, ball mills, roller mills, disc grinders, jet milling and the like. Preferably, a dry milling process is used.

Referring now to FIG. 6, an exemplary wet process or method 400 of producing any one of the formulations described herein is depicted. For example, in step 410, nicotine tartrate is admixed with excipients, such as lactose and leucine, to form a flowable mixture. At step 412, the mixture is atomized. Alternatively, in step 414, nicotine tartrate may be admixed with excipients, such as lactose and leucine, as well as a therapeutic agent, such as menthol, to form a flowable mixture. As contemplated herein, any liquid carrier may be used in the process of producing the solution or suspension. In one embodiment, the liquid carrier is water. Preferably, the liquid carrier is one in which the components of the formulation are either soluble or suspendable. Accordingly, the liquid carrier may be any liquid or liquids with which the components of the formulation, either alone or in combination, form a flowable mixture or suspension which is preferably of a generally uniform composition.

At step 416, the mixture is atomized. At step 420, the mixture is dried, such as via a spray drier. Alternatively, the process may optionally be performed via fluid bed drying, wherein nicotine tartrate can instead be spray dried onto an excipient mixture. At step 430, the resulting nicotine particles are filtered, such as with a sieve, to remove any particles larger than a threshold size value. At step 440, the resulting nicotine particles are filtered again to remove any particles smaller than a threshold size value, resulting in the final dry powder formulation 450. In some embodiments, only one filtering step is needed. In other embodiments, two or more filtering steps are needed. Optionally at step 460, a flavor component may be added to final formulation 450. Step 460 may contain any number of processing steps needed to obtain the desired particle size (e.g., 10-1000 micron) for the flavor component being added.

The flowable mixtures are dried, such as via a spray drier, to produce composite particles of the flowable mixtures that are suitable for delivery to the alveoli and lower airways of a subject. It should be appreciated that there is no limitation to the method of drying the flowable mixtures. While a preferred method utilizes a spray drier, other drying techniques capable of producing appropriately sized particles may be used, such as fluidized bed drying. In one embodiment, the mixture is finely divided via passage through an orifice upon on entry to a spray dryer. In another embodiment, the flowable mixture may be passed through an atomizer, such as a rotary atomizer, to feed the flowable liquid into a spray dryer. Further still, any rate of drying may be used (e.g., slow or rapid rate drying), provided such rate of drying results in the formation of dry particles of the desired size range. Prior to the segregation of the desired particle size of the nicotine-based component, the resultant particles formed via the spray drier may have a particle size from about 0.1 to about 5 micron.

Additional segregation/filtering of selected particle sizes may be performed both in the dry and the wet process. In the wet process, the operating conditions of the spray dryer may be adjusted so to produce particles which are sized so as to be able to travel to the alveoli and smaller airways of the lungs. For example, a rotary atomizer may be operated at a liquid feed rate from about 2 to about 20 ml/min, or from 2 to about 10 ml/min, or from about 2 to about 5 ml/min. Further, the rotary atomizer may be operated from about 10,000 to about 30,000 rpm, from about 15,000 to about 25,000 rpm, or from about 20,000 to about 25,000 rpm. It should be appreciated that particles of various sizes may be obtained by spray drying, and particles having the desired particle size may be more specifically selected when filtered, such as via one or more sieving steps, as described elsewhere herein. The spray dryer may be operated at temperatures sufficiently high to cause the liquid carrier to rapidly evolve without raising the temperature of the sugar and nicotine within the mixture to a point at which these compounds begin to degrade. Accordingly, the spray dryer may be operated with an inlet temperature from about 120° C. to about 170° C., and an outlet temperature from about 70° C. to about 100° C.

It should be appreciated that there is no limitation to the method of drying the flowable mixtures. Examples of methods for drying the flowable mixtures include, but are not limited to, spray drying, vacuum drying, and freeze drying. Further still, any rate of drying may be used (e.g., slow or rapid rate drying), provided such rate of drying results in the formation of dry particles of the desired size range.

As mentioned previously, in the wet process the liquid carrier is dried, such as via a fluidized bed dryer, to produce composite particles of nicotine coated with menthol that are suitable for delivery to the alveoli and lower airways of a subject. It should be appreciated that there is no limitation to the method of drying the flowable mixture. While a preferred method utilizes a fluidized bed dryer, other drying techniques capable of removing the liquid carrier and leaving a uniform menthol coating on the nicotine particles may be used.

As contemplated herein, the particles of the present invention can be produced in relatively narrow size ranges via the use of at least one sieving step. In such an embodiment, the sieving step includes using a sieve corresponding to the minimum or maximum of the desired particle size range to eliminate particles from the mixture that are smaller or bigger than the desired range. For example, to obtain nicotine particles in the range of about 1-5 microns, a mixture of nicotine particles produced using the milling process described herein can be provided. The mixture of nicotine particles will have a size distribution that is dependent on the milling conditions used and/or the characteristics of the input mixture to the mill. The mixture of nicotine particles can first be passed through a 5 micron sieve, wherein substantially all of the particles smaller than 5 microns pass through the sieve and are collected. The particles passing through the sieve can then transferred to a 1 micron sieve, wherein substantially all of the particles greater than 1 micron do not pass through the sieve. The particles greater than 1 micron can be collected from the sieve, wherein the collected particles will be substantially sized in the range of 1-5 microns. Accordingly, such a process can be used to narrow the range of any mixture of particles to any of the desired particle size ranges as described herein throughout In another embodiment, a mixture of particles can be provided that substantially meets either the minimum or maximum criteria of the desired particle size range. For example, if a nicotine particle size range of about 2-5 microns is desired, a mixture of nicotine particles can be provided wherein substantially all of the particles are less than 5 microns. Such a mixture can be produced by modifying the milling conditions, or when the particles are spray dried, by milling the spray dried material to result in a mixture of particles that are generally less than 5 microns. The mixture can then be transferred through a 2 micron sieve, wherein the particles not passing through the sieve are collected, and wherein the collected particles are substantially within the desired 2-3 micron range.

It is contemplated that the percentage of particles falling within the desired particle size range for any of the components of the formulation of the present invention can be dependent on the technique used to produce that component. For example, if the targeted size of the nicotine component is in the range of 2-5 micron, it is understood that greater than 90% of that component will fall within the desired range when using a spray drying production technique on a relatively small scale. However, using a relatively large scale milling production technique may only yield greater than 70% of the nicotine component within such a targeted range.

Kits of the Invention

The present invention also relates to nicotine kits, including, but not limited to, nicotine therapy kits and smoke cessation kits. In one embodiment, the kit may include a plurality of nicotine-based powder formulation doses contained in a sealed storage chamber, such as a capsule or a blister pack. As contemplated herein, at least two of the formulation doses have equal amounts of a total nicotine, but at different nicotine concentrations. In other embodiments, the kit comprises at least two sets of bulk nicotine-based powder having different concentrations of nicotine, and means for measuring set amounts of the powders, such as a scoop or a graduated measuring container, that can be loaded into the storage chamber of a dry powder inhaler.

In another embodiment, the kit includes pre-filled powder capsules for a set course of nicotine therapy or treatment, such as for example a 30 day course of treatment. The capsules can be filled with various amounts of powder of various nicotine concentrations to suit the therapy regimen. In other embodiments, the kit includes instructional materials which describe the steps for a method for nicotine therapy, including, but not limited to, smoke cessation therapy. The steps of the method can include a starting dose, regular doses thereafter, such as multiple daily doses for example, and a final dose, to be administered by means of loading the dry powder formulation doses into a dry powder inhaler.

In another embodiment, the instruction material may instruct the user on a set number of days course of nicotine therapy, in which the daily nicotine dose may be modulated. In one embodiment, the course of nicotine therapy lasts between about 7 days, to about 30 days. In another embodiment, the course of nicotine therapy lasts between about 10 days, to about 45 days. In another embodiment, the course of nicotine therapy lasts between about 15 days, to about 60 days. In another embodiment, the course of nicotine therapy lasts between about 30 days, to about 90 days. In a preferred embodiment, the course of nicotine therapy lasts about 30 days. In another preferred embodiment, the course of nicotine therapy lasts about 45 days. In another preferred embodiment, the course of nicotine therapy lasts about 60 days. In another preferred embodiment, the course of nicotine therapy lasts about 90 days.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A dry powder nicotine formulation comprising nicotine, lactose, and leucine, wherein the concentration of nicotine is between 0.5% and 10%, and wherein the formulation is suitable for inhalation.

2. The formulation of claim 1, wherein the nicotine comprises at least one nicotine salt.

3. The formulation of claim 2, wherein the at least one nicotine salt is nicotine tartrate.

4. The formulation of claim 1, wherein the concentration of nicotine is about 0.5%.

5. The formulation of claim 1, wherein the concentration of nicotine is about 1%.

6. The formulation of claim 1, wherein the concentration of nicotine is about 1.5%.

7. The formulation of claim 1, wherein the concentration of nicotine is about 2%.

8. The formulation of claim 1, wherein the concentration of nicotine is about 2.5%.

9. The formulation of claim 1, wherein the concentration of nicotine is about 3%.

10. The formulation of claim 1, wherein the concentration of nicotine is about 3.5%.

11. The formulation of claim 1, wherein the concentration of nicotine is about 4%.

12. The formulation of claim 1, wherein the concentration of nicotine is about 4.5%.

13. The formulation of claim 1, wherein the concentration of nicotine is about 5%.

14. The formulation of claim 1, wherein the concentration of nicotine is about 10%.

15. The formulation of claim 1, wherein the concentration of lactose is between 50% and 80%.

16. The formulation of claim 1, wherein the concentration of lactose is between 50% and 99%.

17. The formulation of claim 1, wherein the concentration of lactose is at least 50%.

18. The formulation of claim 1, wherein the concentration of leucine is between 0.5% and 10%.

19. The formulation of claim 1, further comprising at least one flavor component.

20. The formulation of claim 1, further comprising at least one therapeutic agent.

21. The formulation of claim 20, wherein the at least one therapeutic agent is a cough suppressant.

22. The formulation of claim 1, further comprising menthol.

23. The formulation of claim 22, wherein the concentration of menthol is between 0.5% and 20%.

24. The formulation of claim 1, further comprising mint.

25. The formulation of claim 24, wherein the concentration of mint is between 0.5% and 20%.

26. A kit for delivering a dry powder nicotine formulation of claim 1, the kit comprising at least an amount of a nicotine formulation comprising nicotine particles, and an instruction material.

\* \* \* \* \*